(12) United States Patent
Nakano et al.

(10) Patent No.: US 7,502,170 B2
(45) Date of Patent: Mar. 10, 2009

(54) ILLUMINATION DEVICE, RECOGNIZING DEVICE WITH THE ILLUMINATION DEVICE, AND PART MOUNTING DEVICE

(75) Inventors: Kazuyuki Nakano, Minami-arupusu (JP); Youichi Tanaka, Ogoori (JP); Hiroyoshi Saitoh, Nakakoma-gun (JP); Junichi Hada, Kurume (JP)

(73) Assignee: Panasonic Corporation, Osaka (JP)

( * ) Notice: Subject to any disclaimer, the term of this patent is extended or adjusted under 35 U.S.C. 154(b) by 860 days.

(21) Appl. No.: 10/523,871

(22) PCT Filed: Jun. 27, 2003

(86) PCT No.: PCT/JP03/08231

§ 371 (c)(1),
(2), (4) Date: Feb. 7, 2005

(87) PCT Pub. No.: WO2004/015363

PCT Pub. Date: Feb. 19, 2004

(65) Prior Publication Data

US 2005/0238222 A1    Oct. 27, 2005

(30) Foreign Application Priority Data

Aug. 8, 2002  (JP) ............................. 2002-231668

(51) Int. Cl.
*G02B 27/10* (2006.01)
*G02B 26/00* (2006.01)

(52) U.S. Cl. ..................... 359/627; 359/290; 359/291

(58) Field of Classification Search ......... 359/251–258, 359/260, 265, 267, 290, 291, 295, 296, 627, 359/707

See application file for complete search history.

(56) References Cited

U.S. PATENT DOCUMENTS 6,324,011 B1 * 11/2001 Higuchi ...................... 359/627
7,271,862 B2 *  9/2007 Matsunaga et al. ............ 349/64

FOREIGN PATENT DOCUMENTS

| JP | 6-72046 | 10/1994 |
|----|---------|---------|
| JP | 672046 | 10/1994 |
| JP | 09-116297 | 5/1997 |
| JP | 11-249020 | 9/1999 |
| JP | 2001-304817 A | 10/2001 |
| JP | 1 182 919 A | 2/2002 |
| JP | 200264296 | 2/2002 |
| JP | 2018041007 | 5/2007 |

* cited by examiner

*Primary Examiner*—Mohammed Hasan
(74) *Attorney, Agent, or Firm*—Pearne & Gordon LLP

(57) ABSTRACT

An illumination apparatus includes a through-hole for detection formed at a center portion, and irradiates diffused light and directional light to an object to be detected. The apparatus includes an annular diffusion plate which diffuses light, a light source disposed annularly, and an annular reflection plate which reflects light from the light source to the side of said object to be detected. The diffusion plate, light source, and reflection plate are disposed in the order from the side of said object to be detected. The diffused light is generated by irradiating light from said light source to the object to be detected through said diffusion plate. Light from said light source is reflected by said reflection plate and then irradiated to the object to be detected.

8 Claims, 13 Drawing Sheets

US 7,502,170 B2

ILLUMINATION DEVICE, RECOGNIZING DEVICE WITH THE ILLUMINATION DEVICE, AND PART MOUNTING DEVICE

TECHNICAL FIELD

This invention relates to an illumination apparatus which, in case of recognizing an object to be detected, such as a mark and an electronic component on a circuit substrate, by use of a sensor such as a camera, illuminates the object to be detected and its vicinity, in order to facilitate execution of recognition, and a recognition apparatus and a component mounting apparatus which were equipped with this.

BACKGROUND TECHNOLOGY

For example, in a component mounting apparatus which mounts electronic components on a circuit substrate, it is generally carried out to image a mark which was disposed on the circuit substrate and to recognized this, for the purpose of position detection etc. of the circuit substrate. In case of carrying out recognition of a mark on the suchlike circuit substrate, an image of the mark and its vicinity is picked up by a camera which was disposed on a mounting head, and that image is processed, and thereby, recognition of the mark is carried out. Then, on the occasion of picking up an image by the camera, an illumination apparatus for illuminating the mark and its vicinity is used. Examples of this kind of a recognition apparatus have been known in JP-A-9-116297 publication and JP-A-11-249020 publication etc.

FIG. 12 is a sectional side view which shows a first example of a recognition apparatus which is described in JP-A-9-116297 publication. This recognition apparatus is such a thing that illumination is carried out by an illumination apparatus 70, and an image is picked up by an image pickup camera 75, and the picked-up image which was obtained is processed by a control section 86, and thereby, a recognition operation of a mark etc. is carried out. The illumination apparatus 70 has a tube type case 71 whose lower surface was opened. At a center portion of a ceiling wall 72 of the case 71, a through-hole 73 is opened, and on the upper side of that through-hole 73, the image pickup camera 75 is disposed through a lens 74. An optic axis of the image pickup camera 73 runs through a center of the through-hole 73. In addition, at a lower position of the through-hole 73 in the case 1, disposed is a half mirror 76 which reflects illumination light to be hereinafter described, which is incident horizontally, toward a vertical-lower side, and transmits light which passes through the through-hole 73 from the vertical-lower side and is incident to the image pickup camera 75.

At a middle stand of an inside of the case 71 on the under side of the half mirror 76, a fixing plate 78 with a through-hole 77, which is coaxial with the through-hole 73, is disposed in such a form that it divides off an inside of the case 71 up and down. On a lower surface of that fixing plate 78, a number of first light sources 79 such as LEDs are disposed annularly, so as to surround and enclose the through-hole 77 at a center of the fixing plate 78. In addition, on a lower end face of the case 71, disposed is a diffusion plate which transmits illumination light from the first light source 79, which was disposed on the fixing plate 78, to a lower side, over diffusing it. At a center of this diffusion plate 80, disposed is a trough-hole 81 which is coaxial with each through-hole 77, 72, which was disposed on the fixing plate 78 and the ceiling wall 72 of the case 71, respectively.

In addition, in a peripheral wall 82 of the case 71, an opening 83 is formed. On an outside of that opening 83, disposed is a second light source 85 such as LED which makes illumination light incident horizontally toward the half mirror 76 in the case 71, through a lens 84. Then, the image pickup camera 75 picks up an image of an object 10 to be detected, which is in such a state that it was illuminated by the illumination apparatus 70, through each through-hole 81. 77, 73 of the diffusion plate 80, the fixing plate 78 and the ceiling wall 72 of the case 71. It is configured that a control section 86 processes this image obtained, to recognize the object 10 to be detected.

In case that an image of the object 10 to be detected is picked up by the image pickup camera 75, which was equipped with the suchlike illumination apparatus 70, to recognize it, the illumination apparatus 70 and the image pickup camera 75 are located on the upper side of the object 1 0 to be detected, and the first light source 79 and the second light source 79 are turned on, and thereby, over illuminating the object 10 to be detected and its vicinity, its image is picked up. In case that it was done, light 88, which was irradiated from the first light source 79, illuminates the object 10 to be detected and its vicinity, widely from periphery, over being diffused by the diffusion plate 80. In addition, light 89, which was irradiated horizontally from the second light source 85 through the lens 84, after it was reflected by the half mirror 76 in the case 71, passes through each through-hole 77, 81 of the fixing plate 78 and the diffusion plate 80, and illuminates the object 10 to be detected and its vicinity, from right above, with a directional characteristic. Therefore, the object 10 to be detected and its vicinity are illuminated by the light from right above and the light from periphery, and thereby, reflected light from the object 10 to be detected and its vicinity passes through each through-hole 81, 77, 73, and is incident to the image pickup camera 75. Thereby, an image of the object 10 to be detected and its vicinity is obtained.

FIG. 13 is a sectional side view which shows a second example of a conventional recognition apparatus which was described in the above-described JP-A-11-249020 publication. In an illumination apparatus 90 of this recognition apparatus, a light path adjustment plate 91 is disposed in lieu of the diffusion plate of FIG. 12, and the half mirror and the second light source are not disposed. Other configurations are almost the same as the thing of FIG. 12, and therefore, identical reference numerals and signs are given to identical constituent elements, and thereby, its explanation is omitted.

The light path adjustment plate 91 refracts light, which the first light source 79 emitted, with different angles, by a small area which was divided into a plurality of pieces in a manner of concentric-strips, and condenses it to a predetermined area where the object 10 to be detected is located. Then, by irradiating light with a plurality of different irradiation angles to the object 10 to be detected, it is configured so as to carry out illumination which is suitable for a surface state of the object 10 to be detected.

In addition, although it is not shown in the figure, the above-described JP-A-11-249020 publication discloses an illumination apparatus which was configured in such a manner that a number of light sources are disposed concentrically, and it is configured so as to be able to adjust an amount of light of the light source with respect to each circumference as a unit, depending on a surface state of an object to be detected, and thereby, it was configured to irradiate illumination light which was suitable for recognition of the object to be detected.

In the meantime, in recent years, such a circuit substrate that gold plating was applied to a substrate mark has increased, and it becomes hard for reflected light from the substrate mark to be incident to an image pickup camera, depending on a style of illuminating, and there was such a case that an image with high contrast is not obtained, and a recognition error occurs.

As to this point, in the illumination apparatus 70 shown in FIG. 12, illumination light along an optic axis of the image pickup camera 75 is applied to the object 10 to be detected, by the half mirror 76, and therefore, it is possible to sure capture reflected light from the object 10 to be detected, by the image pickup camera, and it is possible to obtain an image with high contrast. Therefore, it is possible to solve the above-described problem that a recognition error occurs. However, the half mirror 76 is disposed, and the second light source 85 is allocated on an outside the case 71 through the lens 74, and therefore, there were such problems that a configuration is complex and it is costly, and in addition, an apparatus grows in size and an installation space becomes large.

In addition, in the illumination apparatus 90 shown in FIG. 13, it is possible to sufficiently secure an amount of light which is applied to the object 10 to be detected and its vicinity, but it is not possible to surely solve the problem that it becomes hard for reflected light from the substrate mark to be incident to the image pickup camera, since the object to be detected is irradiated with light from a lateral direction.

In the same manner, the illumination apparatus, which was described in JP-A-11-249020 publication and in which a number of light sources are disposed concentrically and it was configured so as to be able to adjust an amount of light of that light source with respect to each light source group which exists on an identical circumference, can irradiate an object area with illumination light which is optimum on recognizing the object to be detected, but illuminates the object to be detected, with light from a lateral direction, and therefore, can not surely solve the problem that it becomes hard for reflected light from the substrate mark to be incident to the image pickup camera.

The invention aims to provide, in consideration of the above-described circumstance, an illumination apparatus which, even if an object to be detected is of a mirror surface shape and of a concavity and convexity shape, can carry out appropriate illumination which corresponded to it, over trying to realize low cost and miniaturization with a simple configuration, and accordingly enables to recognize an object to be detected without an error, and a recognition apparatus and a component mounting apparatus which were equipped with this.

DISCLOSURE OF THE INVENTION

The above-described aim is accomplished by the following configuration.

(1) An illumination apparatus in which a through-hole for detection is formed at a center portion, and which irradiates diffused light and directional light to an object to be detected, characterized in that at least an annular diffusion plate which diffuses light, light source which were disposed annularly, and an annular reflection plate which reflects light from the light source to the side of the above-described object to be detected, are disposed in the order from the side of the above-described object to be detected, and the above-described diffused light is generated by irradiating light from the above-described light source to the object to be detected through the above-described diffusion plate, and the directional light is generated by reflecting light from the above-described light source by the above-described reflection plate and then, irradiating it to the object to be detected.

In this illumination apparatus, it is possible to irradiate two kinds of light of the directional light and the diffused light, to the object to be detected, and therefore, even if the object to be detected is of a mirror surface shape and of a concavity and convexity shape, it is possible to carry out appropriate illumination which corresponded to it, and accordingly, it is possible to carry out stable detection. In addition, the directional light, which irradiates the object to be detected, is generated without using a half mirror, and by use of the annular light sources and the annular reflection plate, and therefore, it is possible to realize miniaturization with a simple configuration.

(2) The illumination apparatus characterized in the above-described (1) that the light source comprises two kinds of a light source for diffused light and a light source for directional light, and an annular fixing plate, on which the light source for diffused light was disposed on a surface which becomes the side of the above-described object to be detected and the light source for directional light was disposed on the other surface, was disposed between the above-described diffusion plate and the above-described reflection plate.

In this illumination apparatus, two kinds of light sources of the light source for diffused light and the light source for directional light are disposed, and those two kinds of light sources are allocated on front and back surfaces of the fixing plate, and therefore, it is possible to independently control irradiated right from respective light sources, and it is possible to adjust a light amount percentage of the directional light and the diffused light. Therefore, it is possible to make up an appropriate illumination state which accords with a surface state of an object to be detected.

(3) The illumination apparatus characterized in the above-described (2) that the light source for directional light is attached through a flexible elastic pin from the above-described fixing plate.

In this illumination apparatus, the light source for directional light is attached through the flexible elastic pin, and therefore, it is possible to adjust a directional characteristic of irradiated light of the light source for directional light, by bending the elastic pin.

(4) The illumination apparatus characterized in the above-described (2) or (3) that an illumination control section, which individually controls the light source for diffused light and the light source for directional light, is provided, and the illumination control section carries out a switch operation for switching over lighting of each light source, and an adjustment operation for changing illumination intensity of each light source.

In this illumination apparatus, it is possible to individually control lighting and a light amount of the light source for diffused light and the light source for directional light, by the illumination control section, and therefore, it is possible to make up an appropriate illumination state which accords with a surface state of the object to be detected.

(5) The illumination apparatus characterized in any one of the above-described (1) through (3) that the above-described reflection plate is a side end face of an inner surface of the case which provides accommodation for the above-described light source and the above-described diffusion plate.

In this illumination apparatus, the side end face of the case inner surface is used as the reflection plate, and therefore, there is no necessity to daringly make the reflection plate separately and to attach it to the case, and it is possible to realize miniaturization of the case and simplification of the case configuration.

(6) The illumination apparatus characterized in the above-described (5) that at least a side end face of the above-described case inner surface is of a white color or a metal color.

In this illumination apparatus, at least the side end face of the case inner surface is colored by a white color or a metal color, and therefore, it is possible to make a reflection capability of light better.

(7) A recognition apparatus characterized by being equipped with the illumination apparatus which was described in any one of the above-described (1) through (6), an image pickup camera which picks up an image of the object to be detected, which was illuminated by the illumination apparatus, and a control section which caries out recognition processing of the object to be detected, by use of the image which was picked up.

In this recognition apparatus, the object to be detected, which was illuminated by the illumination apparatus, is picked up by the image pickup camera, and the control section applies recognition processing to the picked-up image which was obtained, and thereby, it is possible to recognize the object to be detected, with high accuracy.

(8) A component mounting apparatus which has an absorption nozzle, with which a transfer head, which moves on the upper side of a substrate, was equipped, absorbed and held a component, and transfers the above-described transfer head to mount the component on the substrate at a predetermined position, characterized in that a recognition apparatus which is disposed on the above-described transfer head and detects a mark for alignment which was disposed on the above-described substrate and corrects a mounting position of the above-described component depending on a detection position of the mark for alignment is the recognition apparatus which is described in the above-described (7).

In this component mounting apparatus, even in case that the mark for alignment on the substrate is of a mirror surface such as gold plating, it is possible to detect this mark position with high accuracy, and it is possible to heighten mounting position accuracy of a component.

(9) A component mounting apparatus which has an absorption nozzle, with which a transfer head, which moves on the upper side of a substrate, was equipped, absorbed and held a component, and transfers the above-described transfer head to mount the component on the substrate at a predetermined position, characterized in that a recognition apparatus which is disposed on the lower side of the above-described transfer head and recognizes a component which was absorbed and held by the above-described absorption nozzle is the recognition apparatus which is described in the above-described (7).

In this component mounting apparatus, even if there are a mirror surface and a concavity and convexity surface on a component which is absorbed and held by the absorption nozzle, it is possible to recognize this component with high accuracy, and it is possible to reduce frequency of occurrence of a mounting error.

Figure 1:
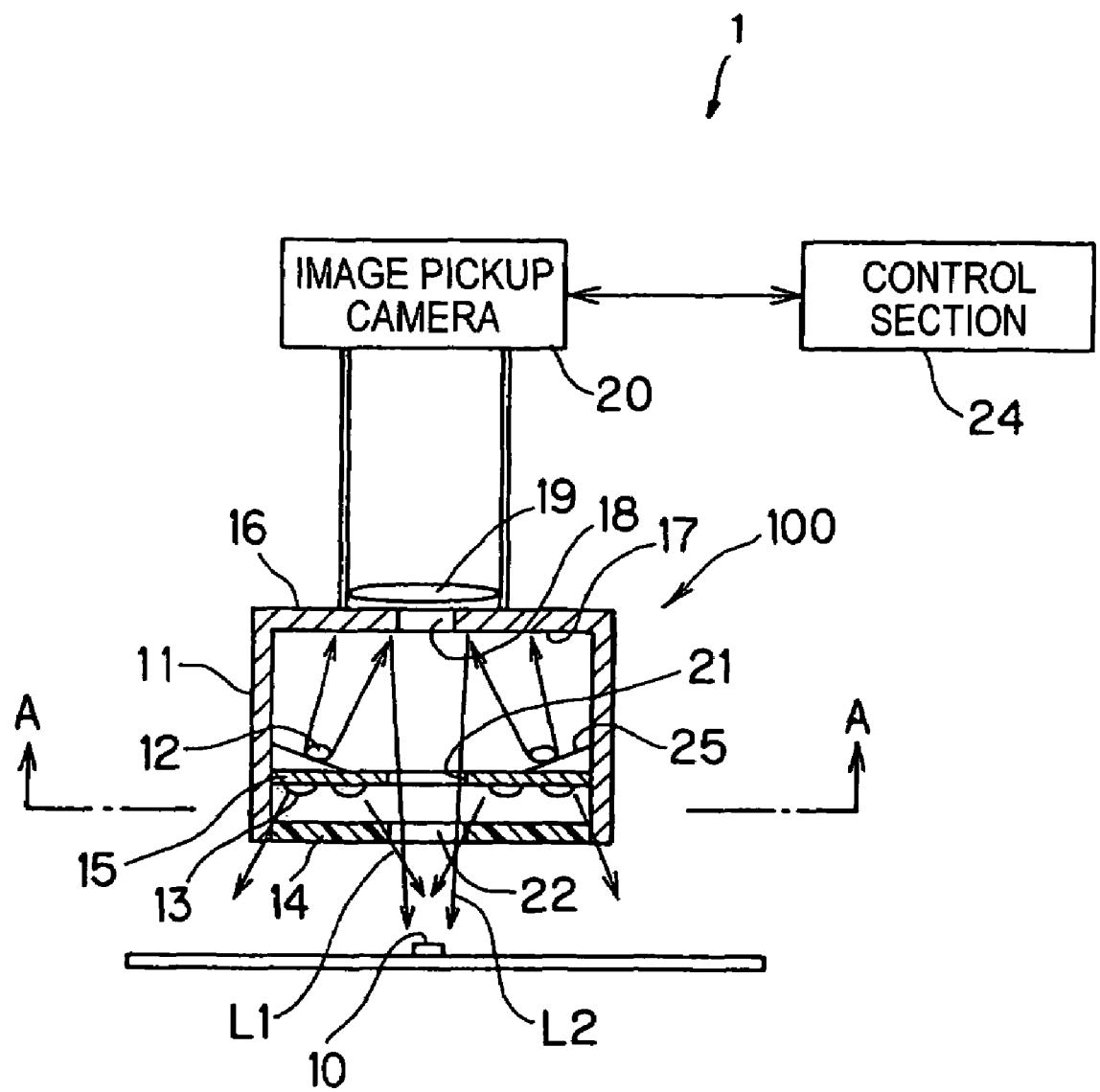
FIG. 1 is a sectional side view of an illumination apparatus of the invention.

Meanwhile, as for reference numerals in the figures, 10 designates an object to be detected, and 11 designates a case, and 12 designates a light source for directional light, and 13 designates a light source for diffused light, and 14 designates a diffusion plate, and 15 designates a fixing plate, and 17 designates a reflection plate, and 18, 21, 22 designate through-holes, and 27 designates an elastic pin, and 30, 31 designate illumination control sections, and 10, 10a, 10b designate objects to be detected, and 100, 200, 300 designate illumination apparatuses, and L1 designates diffused light, and L2 designates directional light.

BEST MODE FOR CARRYING OUT THE INVENTION

Hereinafter, preferred implementation modes of an illumination apparatus which relates to the invention, and a recognition apparatus and a component mounting apparatus which were equipped with this will be described in detail with reference to the drawings.

Figure 2:
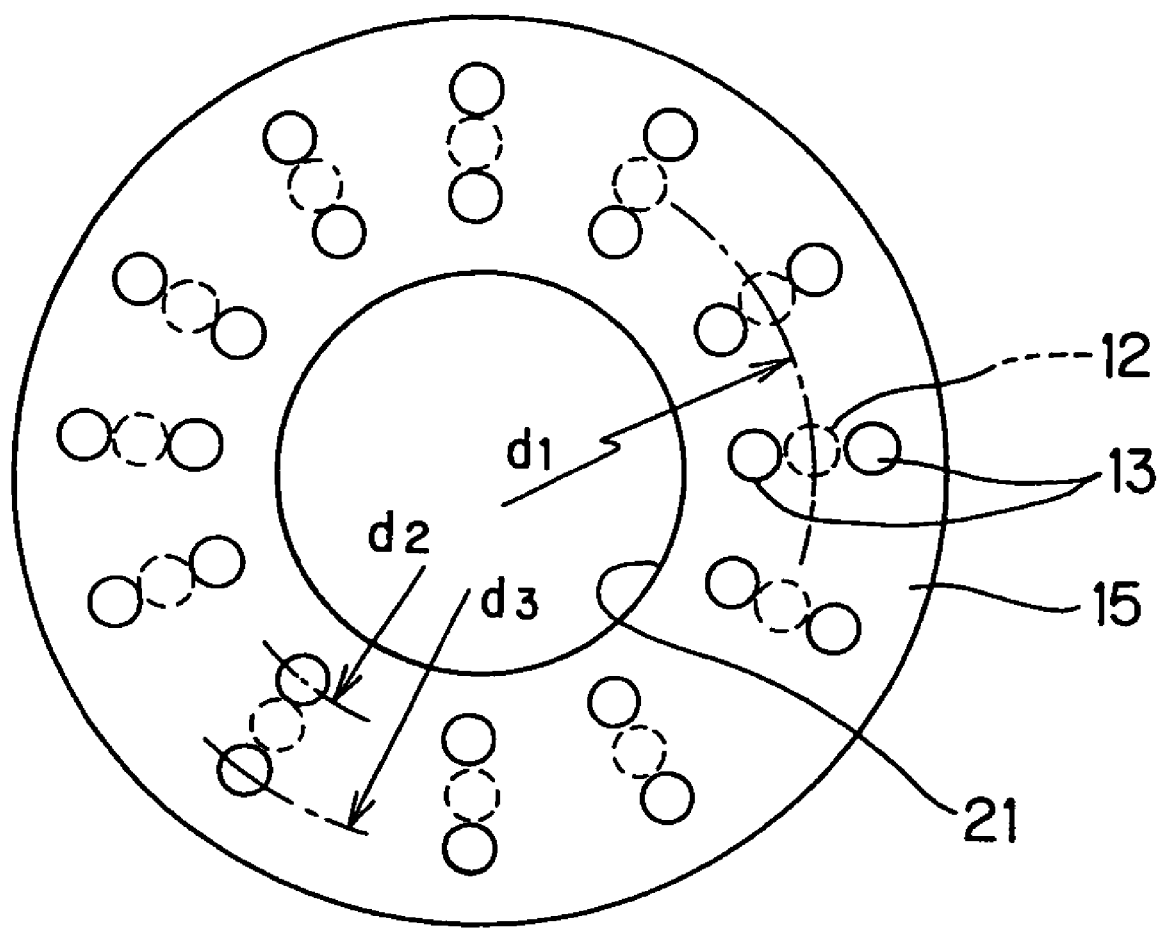
FIG. 2 is a sectional view viewed along A-A arrows of FIG. 1.

FIG. 1 is a side sectional view which shows a major configuration of a recognition which relates to the invention, and FIG. 2 is a sectional view viewed along A-A arrows of FIG. 1.

A recognition apparatus 1 is a thing which picks up an image of an object 10 to be detected, which was illuminated by an illumination apparatus 100, by an image pickup camera 20, and processes the picked-up image which was obtained, by a control section 24, to thereby carry out recognition of the object 10 to be detected.

This illumination apparatus 100 has a case 11 whose lower surface was opened to form a tube type and whose inner surface was unified to a reflective color such as a white color or a metal color. In an inside of the case 11, a number of light sources 12 for directional light and light sources 13 for diffused light, which comprises LEDs etc., and a diffusion plate 14 are contained. The diffusion plate 14 is allocated annularly on a lower end face of the case 11, and on its upper side, allocated is an opaque fixing plate 15 in which the light sources 12 for directional light were attached to an upper surface, and the light sources 13 for diffused light were attached to a lower surface In addition, on an inner surface (side end face) of a ceiling wall 16 of the case 11, formed is a reflection surface as an annular reflection plate 17 for reflecting light, which is irradiated from the light source 12 for directional light, to a lower side. Meanwhile, the annular diffusion plate 14, reflection plate 17 may be also made as a circular ring shape and as a polygon shape.

At a center portion of the ceiling wall 16 which functions as the reflection plate 17, a through-hole 18 as a detection hole is disposed, and on the upper side of that through-hole 18, an image pickup camera (CCD camera etc.) 20 for picking up an image of the object 10 to be detected, is allocated through a lens 19. An optic axis of this image pickup camera 20 runs through a center of the through-hole 18. A video signal of the image pickup camera 20 is inputted to a control section 24 which has an image recognition function, and is image-processed here, and thereby, the object 10 to be detected is recognized by the image which was picked up. The lens 19 is a thing which adjusts an expansion rate of the object 10 to be detected- Meanwhile, it is also possible to use another optical sensor, in lieu of the image pickup camera 20.

In addition, reflected light from the object 10 to be detected is captured by the image pickup camera 20 through the diffusion plate 14 and the fixing plate 15, through-holes 21, 22, which are coaxial with the through-hole 18 of the case 11, are disposed also at center portions of the fixing plate 15 and the diffusion plate 14. The, the light sources 12 for directional light and the light sources 13 for diffused light are allocated annularly on upper and lower surfaces of the fixing plate 15 so as to surround the center through-hole 21. As shown in FIG. 2, the light sources 12 for directional light are allocated annularly on a circumference with a radius d1, which is coaxial with the through-hole 21, and the light sources 13 for diffused light are allocated annularly on two circumferences with radiuses d2 and d3, which are coaxial with the through-hole 21. Meanwhile, allocation of each light source is not limited this, and it is all right if it is allocation by which it is possible to irradiate light uniformly.

The diffusion plate 14 fulfills a function for transmitting illumination light from the first light sources 13 for diffused light, to a lower side, over diffusing it. In addition, the reflection plate 17 fulfills a function for reflecting light from the light source 12 for directional light to a lower side, and generating directional light L1 which passes through the thoughholes 21, 22 of the fixing plate 15 and the diffusion plate 14 and is irradiated to the object 10 to be detected. Meanwhile, in order to orient light which was reflected by the reflection plate 17, effectively to the object 10 to be detected, passing through the through-holes 21, 22, the light sources 12 for directional light are attached to the fixing plate 15 through a tilting table 25.

Next, working of this recognition apparatus 1 will be described.

In case that an image of the object 10 to be detected is picked up by the image pickup camera 20 by use of the suchlike illumination apparatus 100, to carry out recognition processing by the picked-up image which was obtained, the illumination apparatus 100 and the image pickup camera 20 are allocated on the upper side of the object 10 to be detected, and two kinds of light sources of the light source 12 for directional light and the light source 13 for diffused light are turned on at the same time, or any one of them is turned on, and thereby, an image of the object 10 to be detected and its vicinity is picked up over illuminating it. In that case, in order to heighten a recognition rate and recognition accuracy, there is a necessity to apply illumination light with appropriate light amount and incident angle, to the object 10 to be detected.

As to this point, according to this illumination apparatus 100, light, which was irradiated from the light source 13 for diffused light, becomes diffused light L1 on the occasion of transmitting the diffusion plate 14, and illuminates widely the object 10 to be detected and its vicinity from periphery. In addition, light, which was irradiated from the light source 12 for directional light, is reflected by the reflection plate 17 to become directional light L2, and it passes through each through-hole 21, 22 of the fixing plate 15 and the diffusion plate 14, and illuminates the object 10 to be detected and its vicinity from nearly right above. Therefore, by the directional light L2 from right above and the diffused light L2 from periphery, the object 10 to be detected is irradiated with light with different incident angles. As a result of that, reflected light from the object 10 to be detected and its vicinity passes through each through-hole 21, 22, 18, and is incident to the image pick up camera 20, and thereby, an image with clear contrast is obtained. Therefore, a recognition result by the control section 24 becomes good, and a recognition rate and recognition accuracy are improved.

Figure 3:
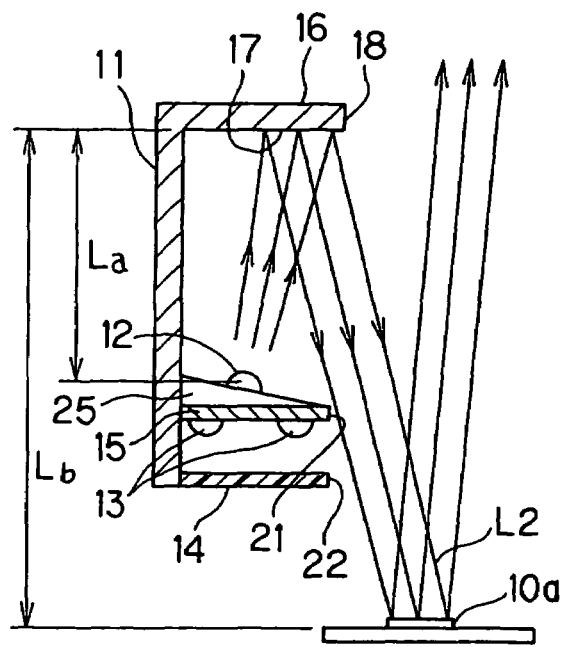
FIG. 3 is an explanatory view which explains a light path of illumination light.
Figure 3:
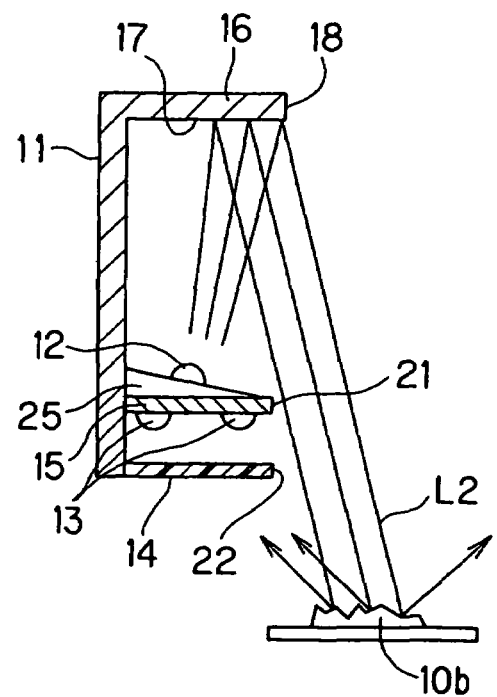
Figure 3:
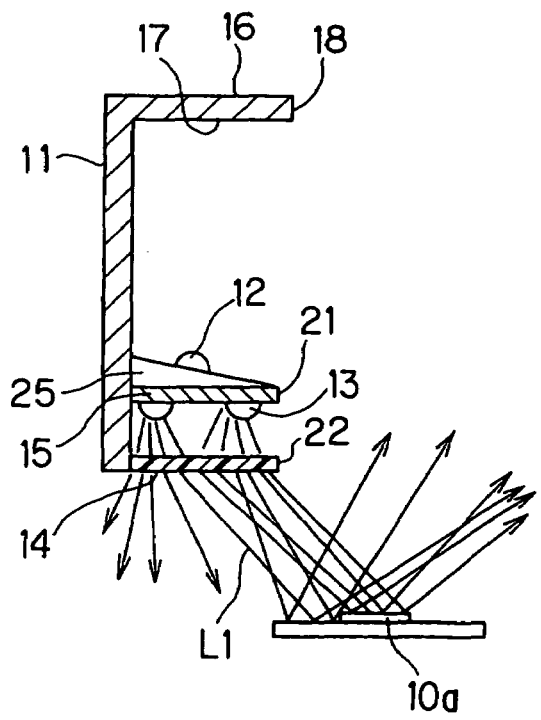
Figure 3:
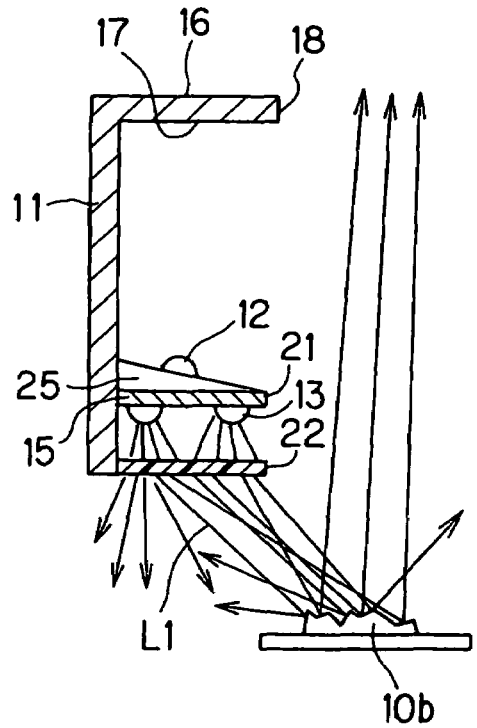

FIG. 3 is an explanatory view for explaining a light path of illumination light by the illumination apparatus 100.

FIG. 3(*a*) shows a situation at the time that the light source 12 for directional light is turned on and the mirror surface shaped object 10 to be detected was illuminated. Light (directional light L2) from the light source 12 for directional light is reflected once by the reflection plate 17 of a ceiling inner surface of the case 11, and irradiates an object 10*a* to be detected. On this account, the longer a distance La between the light source 12 for directional light and the reflection plate 17, and a distance Lb between the reflection plate 17 and the object 10*a* to be detected, are, the higher a level of a directional characteristic becomes, and more favorable directional illumination light is obtained. Reflected light from the mirror surface shaped object 10*a* to be detected is introduced into the image pickup camera 20 through the through-holes 22, 21, 18 of the illumination apparatus 100. Meanwhile, so as for reflected light from the object 10*a* to be detected, to enter into the through-holes 22, 21, 18, positions of the reflection plate 17 and the light source 12 for directional light are adjusted arbitrarily.

FIG. 3(*b*) shows a situation at the time that the light source 12 for directional light is turned on, and a concave and convex surface shaped object 10*b* to be detected was illuminated. Light (directional light L2) from the light source 12 for directional light is diffused by a concave and convex surface of the object 10*b* to be detected, and it seldom or never enter into the through-holes 22, 21 of the illumination apparatus 100.

FIG. 3(*c*) shows a situation at the time that the light source 13 for diffused light is turned on, and the mirror surface shaped object 10*a* to be detected was illuminated. A light path of light from the light source 13 for diffused light is diffused by the diffusion plate 14, and it becomes the diffused light L1, and the object 10*a* to be detected is irradiated by a random incident angle. On that account, reflected light from the object 10*a* to be detected seldom or never enter into the through-holes 22, 21 of the illumination apparatus 100.

FIG. 3(*d*) shows a situation at the time that the light source 13 for diffused light is turned on, and the concave and convex surface shaped object 10*b* to be detected was illuminated. The diffused light L1, which is irradiated from the light source 13 for diffused light through the diffusion plate 14, is reflected by the concave and convex surface of the object 10*b* to be detected, and a part thereof is introduced into the image pickup camera 20 through the through-holes 22, 21, 18 of the illumination apparatus 100.

Therefore, by having the light source 13 for diffused light and the light source 12 for directional light turned on, it becomes possible to detect reflected light from the objects 10a, 10b to be detected, regardless of surface states of the object 10a, 10b to be detected, as shown in FIGS. 3(a),(d), and even if they are of a mirror shape or a concave and convex surface, it is possible to detect by the image pickup camera 20.

Figure 4:
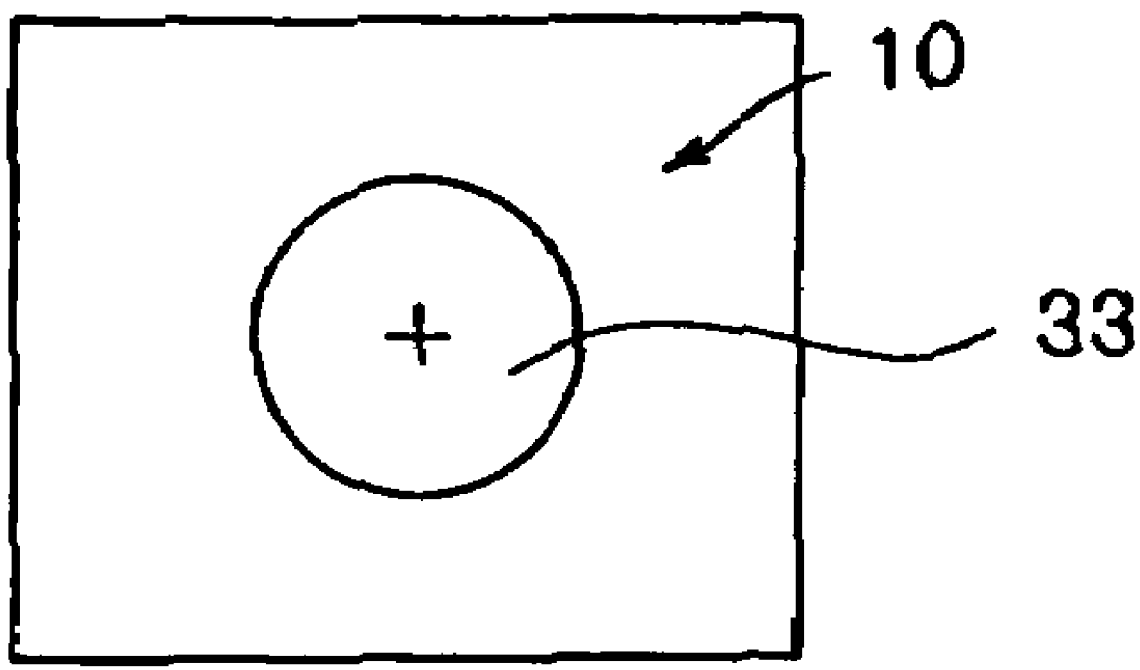
FIG. 4 is an explanatory view which shows a pickup image of a substrate mark by an image pickup camera.

FIG. 4 is one example of a picked-up image of a substrate mark by the image pickup camera. For example, in case of picking up an image of a substrate mark 33 which is of a mirror surface shape as the object 10 to be detected, reflected light from the object 10 to be detected is surely introduced into the image pickup camera 20, and therefore, an image with a definite outline is obtained in a high contrast state. By this, it is possible to easily obtain a center position ("+" mark position in the figure) of the substrate mark 33 by image processing, and recognition processing is carried out with necessary and sufficient accuracy.

Figure 5:
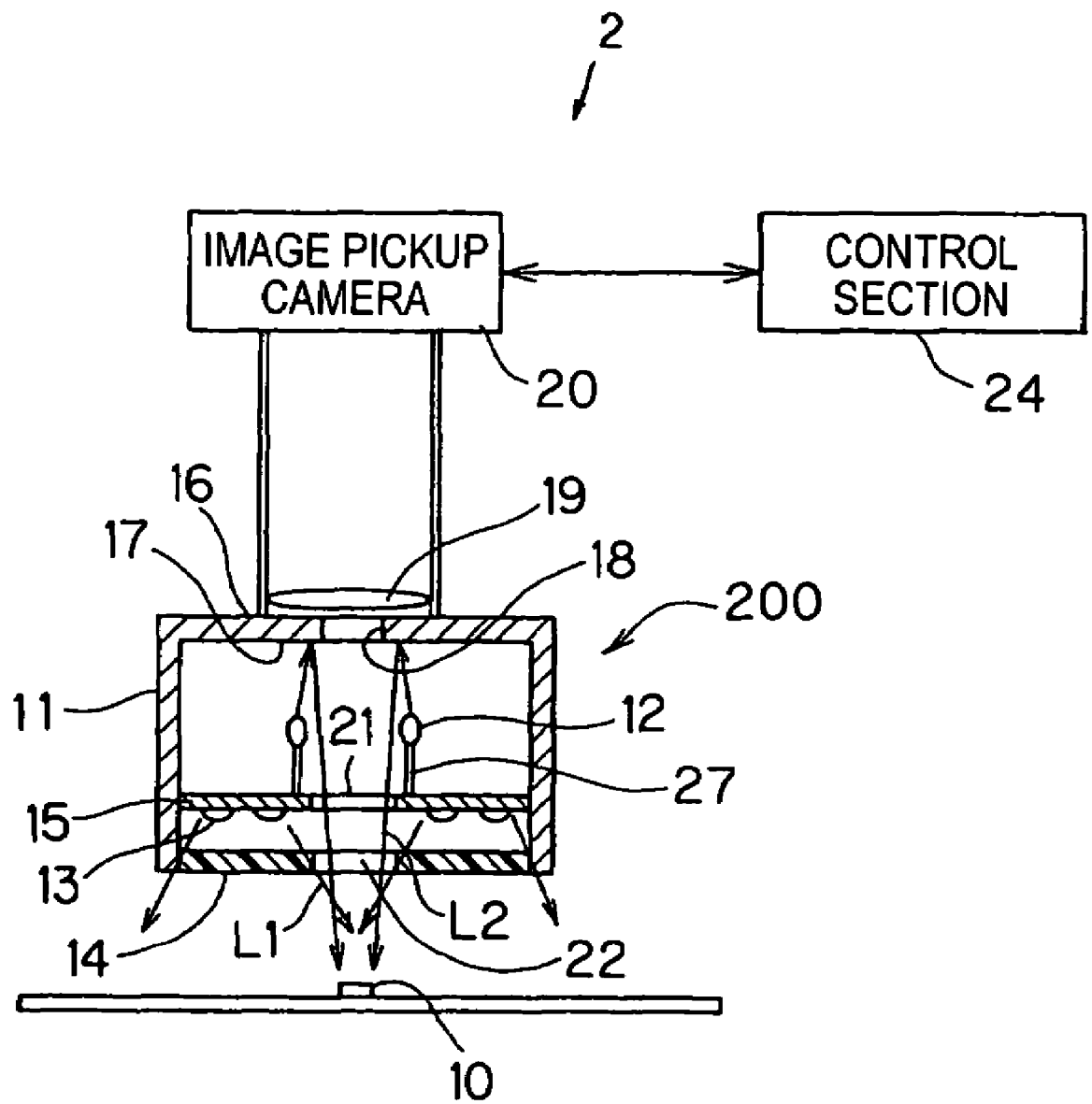
FIG. 5 is a side sectional view of an illumination apparatus in which a light source for directional light was disposed through an elastic pin.
Figure 6:
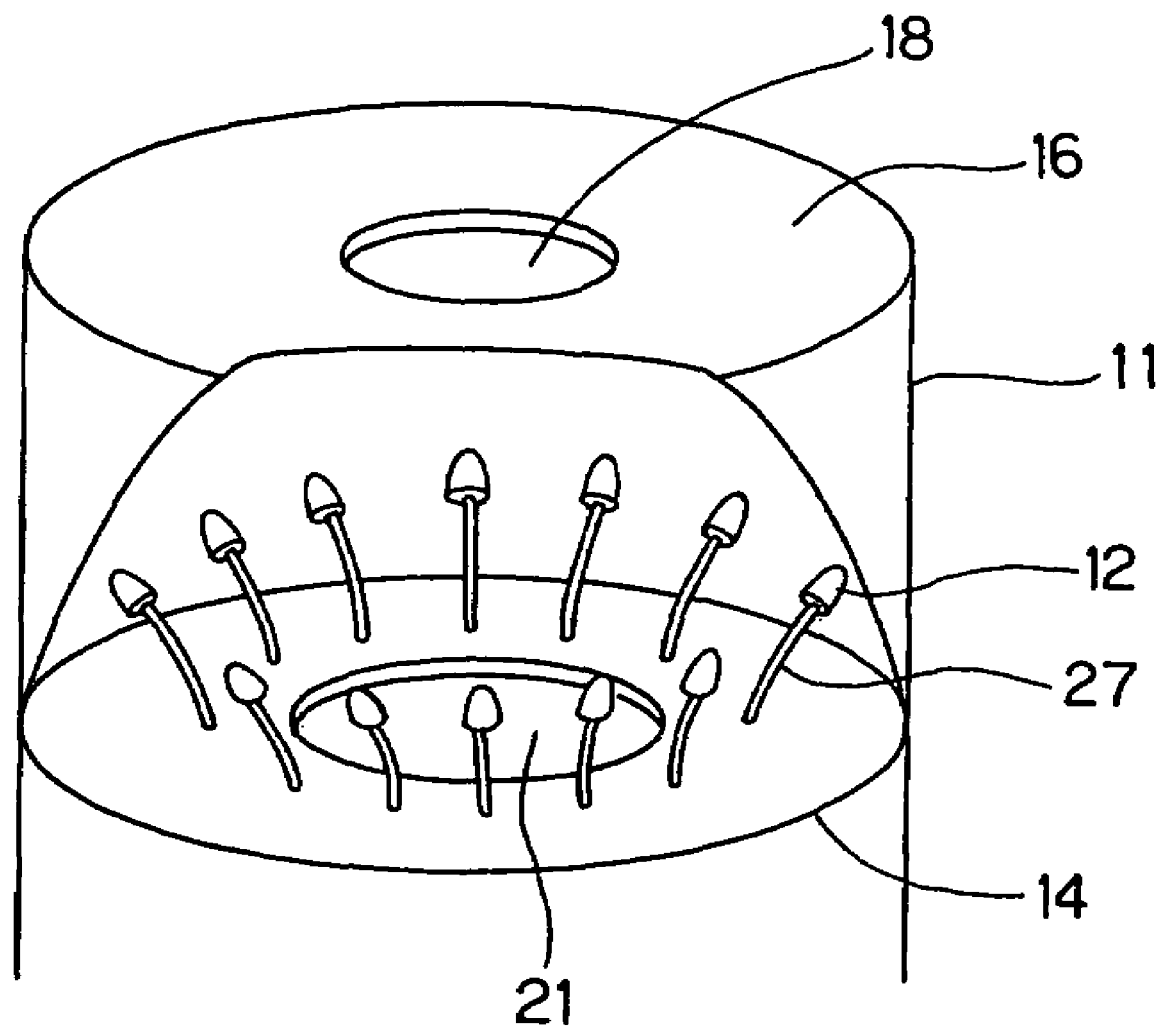
FIG. 6 is an enlarged perspective view which shows a substantial part configuration of the illumination apparatus shown in FIG. 5.

FIG. 5 is a side sectional view which shows a recognition apparatus of a second implementation mode of the invention, and FIG. 6 is an enlarged perspective view which shows a substantial part configuration of an illumination apparatus.

As for this illumination apparatus 2, a portion of the illumination apparatus of the recognition apparatus in the above-described first implementation mode is simply different, and other configuration is the same. On that account, identical reference numerals and signs are given to identical constituent elements, and thereby, its explanation is omitted.

In an illumination apparatus 200, light sources 12 for directional light, which were allocated on an upper surface side of a fixing plate 15, are attached to the fixing plate 15 through flexible elastic pins 27. A configuration other than that is the same as in the illumination apparatus 100 shown in FIG. 1. As above, by attaching the light source 12 for directional light through the elastic pin 27, it is possible to voluntarily adjust a direction of the light source 12 for directional light, i.e., an irradiation direction. Therefore, it is possible to delicately adjust an irradiation angle of the directional light L2 to the object 10 to be detected, by bending the elastic pin 27, as shown in FIG. 6.

Figure 7:
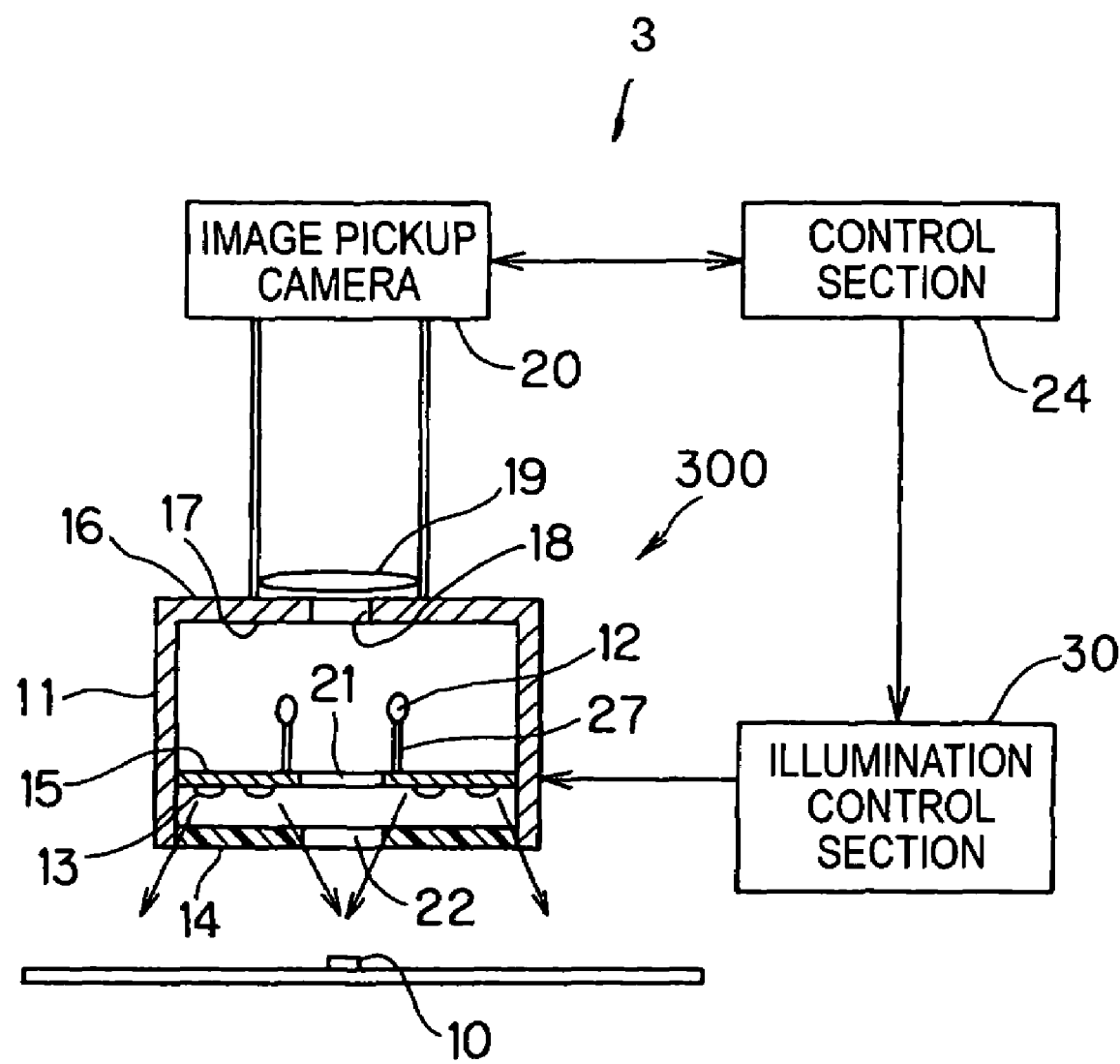
FIG. 7 is a side sectional view of an illumination apparatus in which illumination light was made to be switchable at the time of diffused light illumination.
Figure 8:
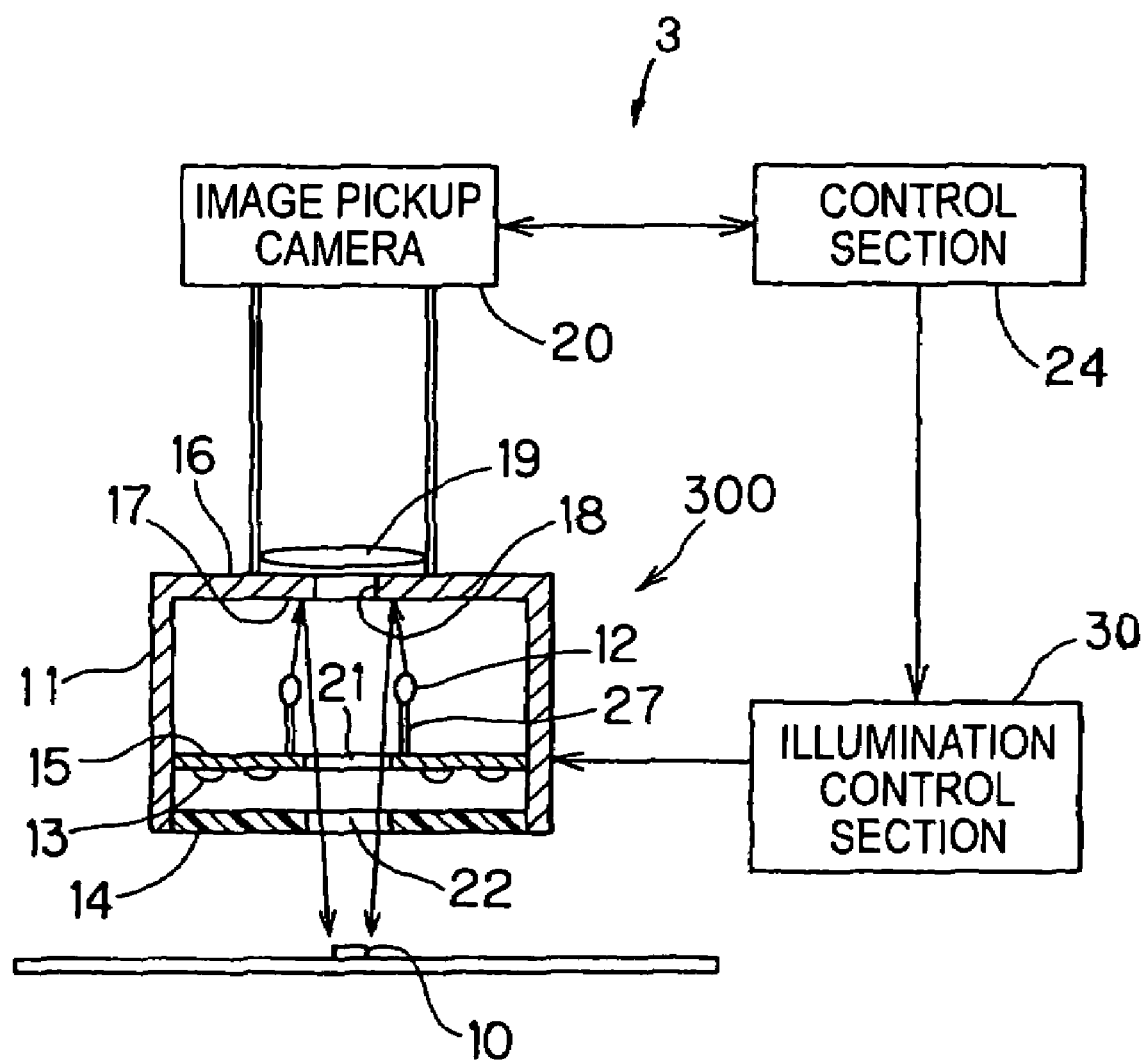
FIG. 8 is a side sectional view of an illumination apparatus in which illumination light was made to be switchable at the time of directional light illumination.

FIG. 7 is a side sectional view of an illumination apparatus of a third implementation mode of the invention at the time of diffused light illumination. FIG. 8 is a side sectional view of the same illumination apparatus at the time of directional light illumination.

A recognition apparatus 3 in this implementation mode is equipped with an illumination control section 30 for individually controlling light sources 13 for diffused light, and other configuration is the same as the configuration of the second implementation mode. This illumination control section 30 carries out a switch operation for switching over lighting of light sources 12 for directional light and light sources 13 for diffused light, and an adjustment operation for changing illumination intensity of each light source 12, 13. Therefore, in this illumination apparatus 300, it is possible to carry out appropriate illumination control depending on a surface state of an object 10 to be detected.

Meanwhile, the illumination control section 30 may adjust local strength and weakness of illumination light to an illumination direction, or allocation of strength and weakness between directional light and diffused light, etc., light amount balance etc., in addition to switching over the light sources 12, 13 depending on a surface state of the object 10 to be detected.

Figure 9:
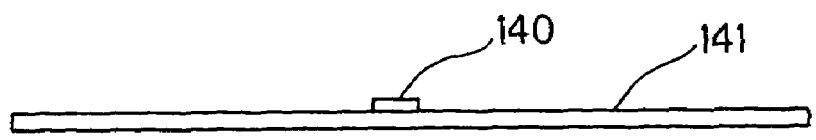
FIG. 9 is an explanatory view of an object to be illuminated, to which the illumination apparatus of the invention is applicable.
Figure 9:
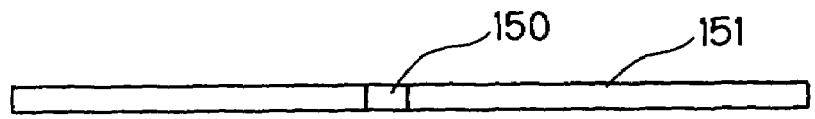
Figure 9:

In addition, as a machine which is equipped with the recognition apparatuses of the invention together with the image pickup camera, a component mounting apparatus, a cream solder printing apparatus, an adhesive agent coating apparatus, etc. are cited as examples. As an object to be detected as an illumination object in that case, there is, for example, an example as in FIG. 9. (a) In the component mounting apparatus, it is a substrate mark 140 on a circuit substrate 141, or a component which was absorbed and held by a component absorption nozzle, and (b) in the cream solder printing apparatus, it is a positioning hole 150 on a screen 151, and (c) in the adhesive agent coating apparatus, it is an adhesive agent 160 on a while color paper 161.

Here, one example, in which the above-described recognition apparatus was applied to a component mounting apparatus, will be hereinafter described.

Figure 10:
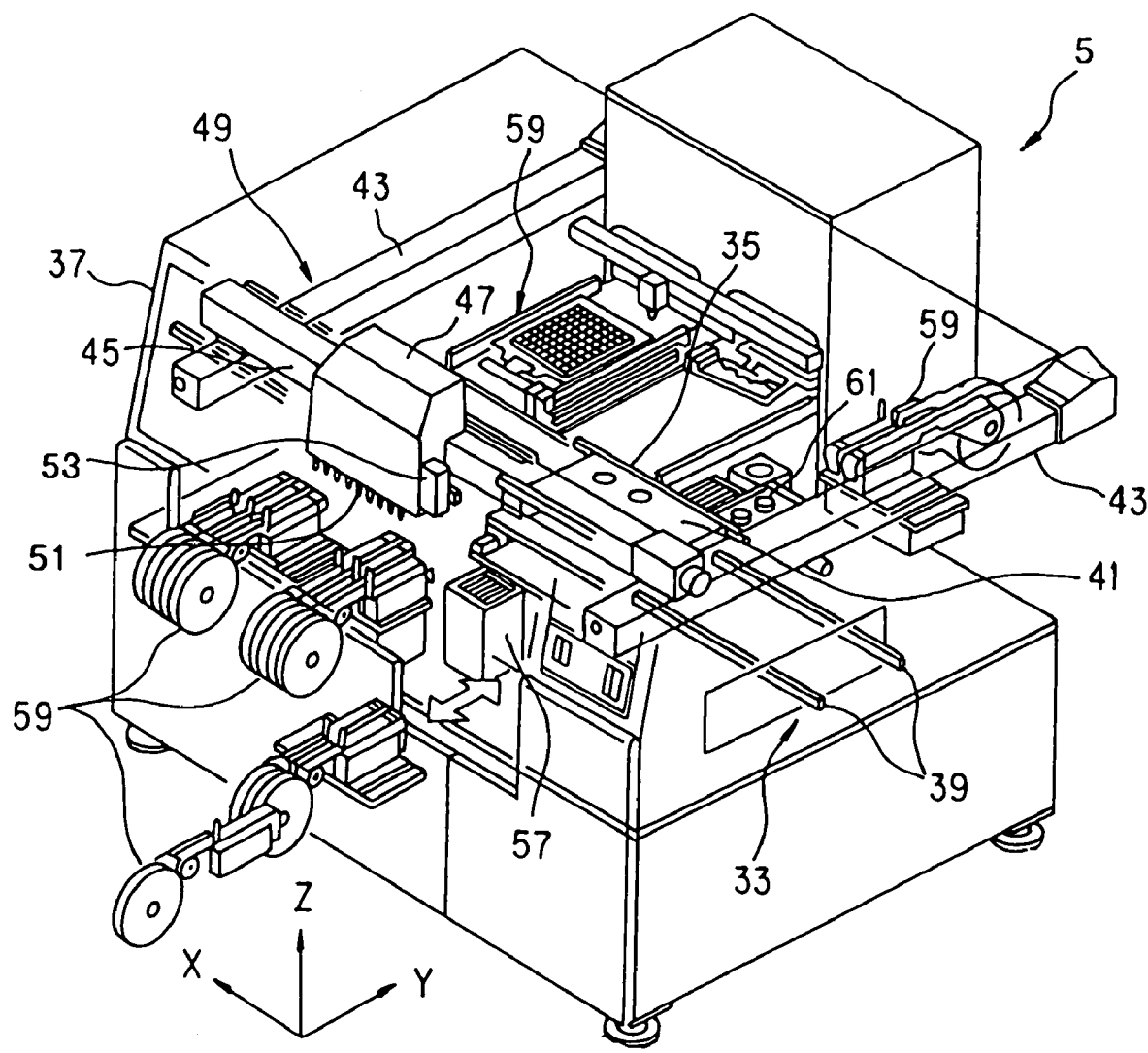
FIG. 10 is a perspective view which represented a schematic configuration of a component mounting apparatus.
Figure 11:
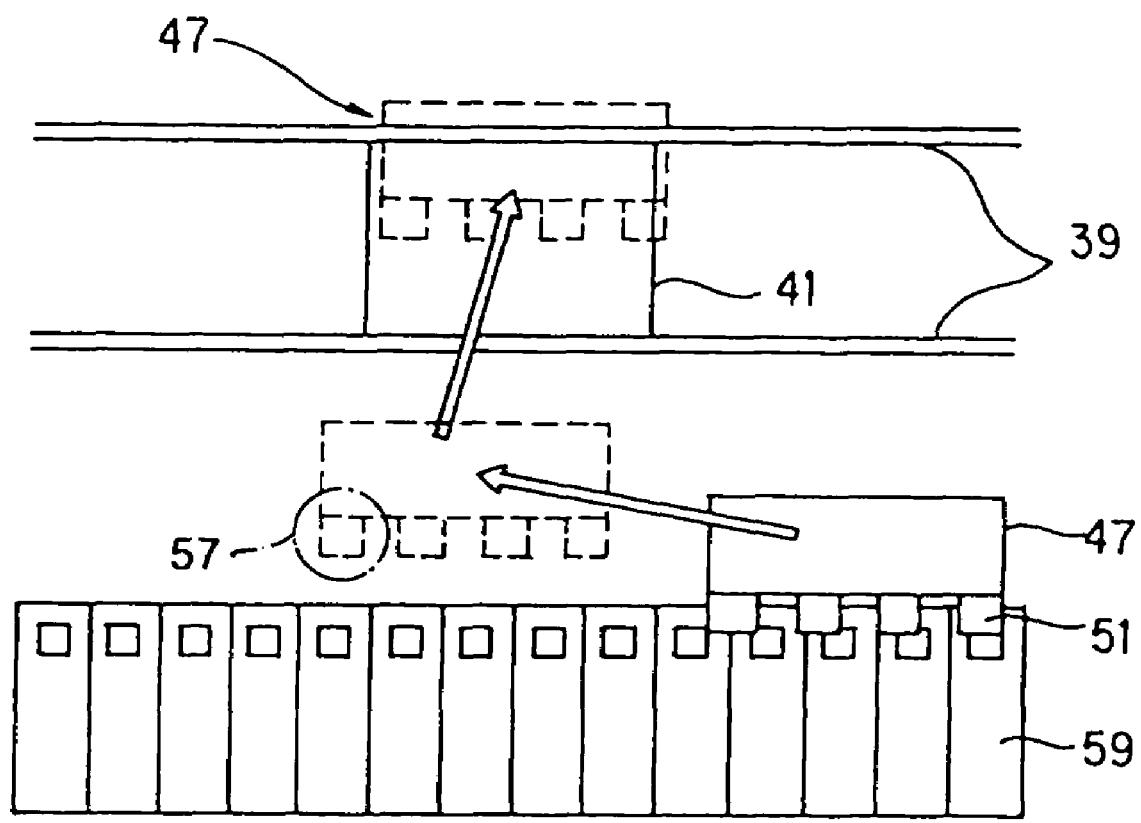
FIG. 11 is an operation explanatory view of a transfer head.
Figure 12:
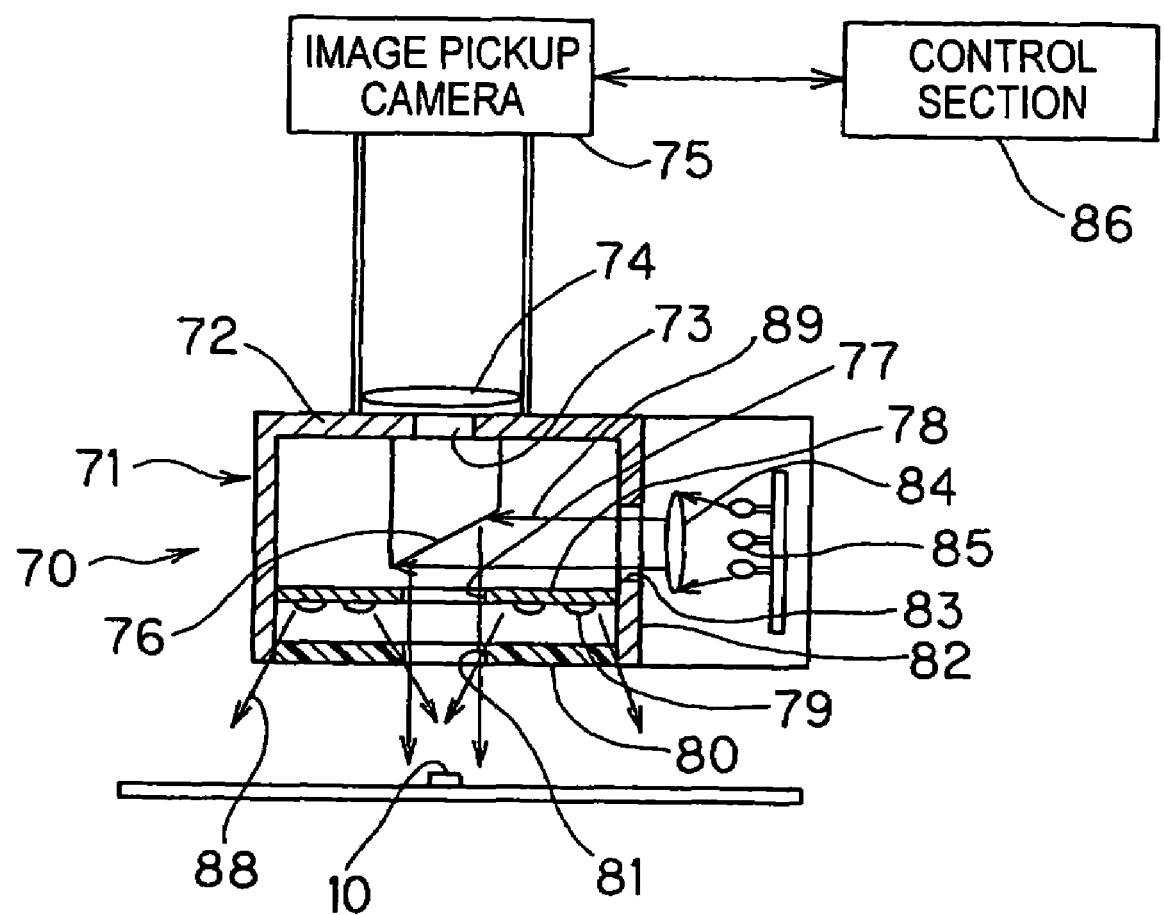
FIG. 12 is a side sectional view which shows an example of a conventional illumination apparatus.
Figure 13:
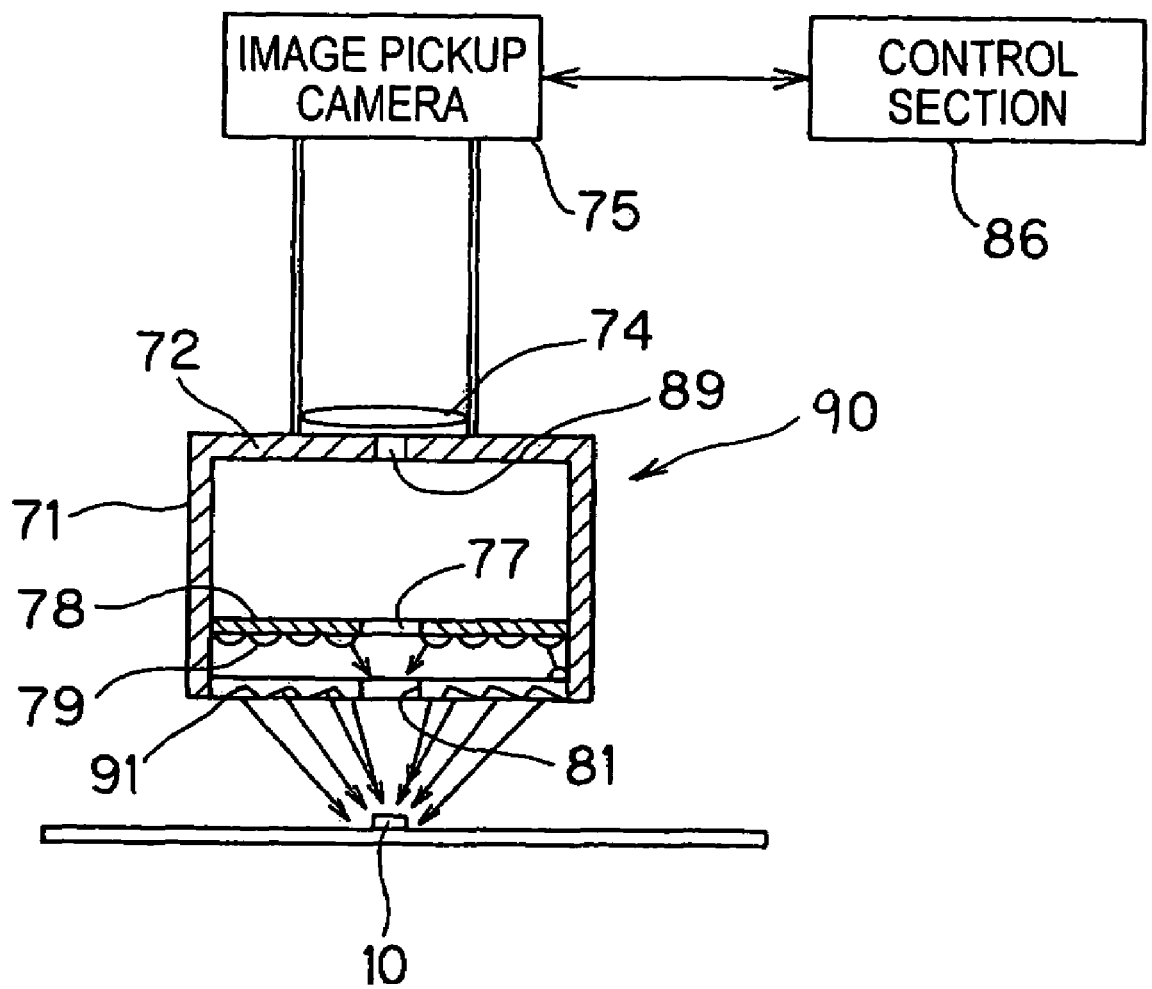
FIG. 13 is a side sectional view which shows another example of the conventional illumination apparatus.

FIG. 10 is a perspective view which represented a schematic configuration of a component mounting apparatus, and FIG. 11 is an operation explanatory view of a transfer head.

As shown in FIG. 10, on a base table of a component mounting apparatus 5, a carrier section, which comprises a pair of guide rails 39, is disposed across a substrate holding section 35, and an unloader section 37. By synchronous drive of a carrier belt with which this guide rail 39 was equipped, a circuit substrate 41 is carried from a loader section 33 at one end side to the substrate holding section 35, the unloader section 37 at the other end side.

On the base table, Y axis robots 43, 43 are disposed, and between these two Y axis robots 43, 43, an X axis robot 45 is suspended, and by drive of the Y axis robots 43, 43, the X axis robot 45 can go forward and backward in a Y axis direction In addition, a transfer head 47 is attached to the X axis robot 45, and the transfer head 47 can go forward and backward in an X axis direction, and by this, the transfer head 47 can move in an X-Y plane.

The transfer head 47, which is mounted on an XY robot 49 which comprises the X axis robot 45, the Y axis robots 43, 43 and moves universally on the X-Y plane, is configured so as to be able to absorb a desired electronic component, from a component supply section 59 to which electronic components such as, for example, resistor chips and chip capacitors are supplied, through an absorption nozzle 52 which was attached to a component mounting head 51, and to mount it at a component mounting position of the circuit substrate 41. The suchlike mounting operation of an electronic component is controlled on the basis of a mounting program which was set up in advance.

On the transfer head 47, an image pickup camera and an illumination apparatus of a recognition apparatus (any one of the above-described recognition apparatuses 1 through 3) are mounted, and the recognition apparatus 53 detects an amount of reflected light of light which was irradiated at a position of an object to be detected. This image pickup camera is connected to a control section, and the control section carries out recognition processing of presence or absence of the object to be detected and a coordinate, depending on a detection result from this image pickup camera. In short, the recognition apparatus 53 is positioned at an arbitrary position, together with the transfer head 47 which is moved by the XY robot 49, and detects a mark of the absorption nozzle 52 which is the object to be detected, likewise, a production management mark (position correction mark, NG mark etc.) of the circuit substrate 41 which is the object to be detected.

In addition, on the side part of the guide rail 391, disposed is a component recognition apparatus 57 (any one of the above-described recognition apparatuses 1 thorough 3) for detecting a two-dimensional displacement (absorption posture) of an electronic component which was absorbed by the component mounting head 51, and for judging good or bad (e.g., failure such as bending of a lead) of an electronic component which was absorbed by the component mounting head 51. The detected displacement is used for generating data for correcting the transfer head 47 side so as to be canceled at the time of mounting. The component recognition apparatus 57 is allocated on a lower side of a head moving path, and picks up images of plural electronic components which were absorbed and held by the component mounting head 51 at one time, during a period of high speed movement from the component supply section 59 to a mounting position, without stopping the transfer head 47.

Here, a schematic component mounting operation of the component mounting apparatus 5 will be described.

When the circuit substrate 41, which was carried in from the loader section 33, is carried to a predetermined mounting position, the transfer head 47 moves in the XY plane by the XY robot 49, and as shown in FIG. 11, absorbs a desired component from the component supply section 59, and moves on the component recognition apparatus 57, and confirms an absorption state of an electronic component, and carries out good or bad judgment and a correction operation. After that, an electronic component is mounted at a predetermined position of the circuit substrate 41. On this occasion, the transfer head 47 detects substrate marks for alignment which were disposed at diagonal positions, respectively, by an image pickup camera and an illumination apparatus of the recognition apparatus 53, and obtains fixed position information of the circuit substrate 41, and mounts an electronic component over carrying out correction of a mounting position.

In this way, the component mounting apparatus 5 completes mounting of an electronic component to the circuit substrate 41, by repetition of absorption of an electronic component, and mounting to the circuit board 41. The component mounting apparatus 5 carries out the circuit substrate 41 for which mounting was completed, from the mounting position to the unloader section 37, and in addition, carries a new circuit substrate 41 in the loader section 33, and repeats the above-described operation.

As described above, according to this component mounting apparatus 5, by applying a recognition apparatus of the invention to the recognition apparatus 53 and the component recognition apparatus 57, it becomes possible to select illumination depending on an object to be detected, and even if gold plating is applied to a substrate mark to realize a mirror surface, it is possible to detect this substrate mark with high accuracy, and it is possible to improve mounting position accuracy of a component. In addition, recognition accuracy of a component which was absorbed and held by the absorption nozzle is improved, and it is possible to reduce frequency of occurrence of a mounting error.

INDUSTRIAL APPLICABILITY

According to an illumination apparatus of the invention, and a recognition apparatus and a component mounting apparatus which used this, it was configured so as to be able to irradiate two kinds of light of directional light and diffused light to an object to be detected, and therefore, even if the object to be detected is of a mirror surface shape or of a concavity and convexity shape, it is possible to carry out appropriate illumination which corresponded to it, and therefore, it is possible to detect an object to be detected, stably. Furthermore, directional light is generated by use of annular light sources and an annular reflection plate, without using a half mirror etc., and therefore, it is possible to realize miniaturization with a simple configuration, and to realize cost down.

The invention claimed is:

1. An illumination apparatus in which a through-hole for detection is formed at a center portion and which irradiates diffused light and directional light to an object to be detected, characterized in that at least an annular diffusion plate which diffuses light, light sources which are allocated annularly, and an annular reflection plate which reflects light from the light sources to said object to be detected, are respectively allocated in order from a side of said object to be detected, and the diffused light is generated by irradiating light from said light sources to the object to be detected through said diffusion plate, and the directional light is generated by reflecting light from said light sources by said reflection plate and then irradiating it to the object to be detected, and the light sources include a light source for diffused light and a light source for directional light, and an annular fixing plate on which the light source for diffused light is disposed on a surface facing said object to be detected, and the light source for directional light is disposed on another surface of the fixing plate and between said diffusion plate and said reflection plate.

2. The illumination apparatus as set forth in claim 1, characterized in that the light source for directional light is attached through a flexible elastic pin from said fixing plate.

3. The illumination apparatus as set forth in claim 1 or 2, characterized in that an illumination control section, which individually controls the light source for diffused light and the light source for directional light, is provided, and the illumination control section carries out a switch operation for switching over lighting of each light source, and an adjustment operation for changing illumination intensity of each light source.

4. The illumination apparatus as set forth in claim 3, characterized in that said reflection plate is a side end face of an inner surface of a case which provides accommodation for said light sources and said diffusion plate.

5. The illumination apparatus as set forth in claim 4, characterized that at least the side end face of said case inner surface is of a white color or a metal color.

6. A recognition apparatus characterized by being equipped with the illumination apparatus as set forth in claim 1, an image pickup camera which picks up an image of the object to be detected, which was illuminated by the illumination apparatus, and a control section which carries out recognition processing of the object to be detected, by use of the image which was picked up.

7. A component mounting apparatus which has an absorption nozzle, with which a transfer head, which moves on an upper side of a substrate, was equipped, absorbed and held a component, and transfers said transfer head to mount the component on the substrate at a predetermined position,
characterized in that a recognition apparatus which is disposed on said transfer head and detects a mark for alignment which was disposed on said substrate and corrects a mounting position of said component depending on a detection position of the mark for alignment is the recognition apparatus which is described in claim 6.

8. A component mounting apparatus which has an absorption nozzle, with which a transfer head, which moves on an upper side of a substrate, was equipped, absorbed and held a component, and transfers said transfer head to mount the component on the substrate at a predetermined position,
characterized in that a recognition apparatus which is disposed on a lower side of said transfer head and recognizes a component which was absorbed and held by said absorption nozzle is the recognition apparatus which is described in claim 6.

* * * * *

UNITED STATES PATENT AND TRADEMARK OFFICE
CERTIFICATE OF CORRECTION

| | | |
|---|---|---|
| PATENT NO. | : 7,502,170 B2 | Page 1 of 3 |
| APPLICATION NO. | : 10/523871 | |
| DATED | : March 10, 2009 | |
| INVENTOR(S) | : Kazuyuki Nakano et al. | |

It is certified that error appears in the above-identified patent and that said Letters Patent is hereby corrected as shown below:

In Column 3, line 67, please complete the paragraph by inserting --and the above-described light source comprises two kinds of a light source for diffused light and a light source for directional light, and an annular fixing plate, on which the light source for diffused light was allocated on a surface which becomes the above-described object to be detected side and the light source for directional side was allocated on the other surface, was disposed between the above-described diffusion plate and the above-described reflection plate.--.

In Column 4, line 1, please delete the text starting with "In" and continuing up to line 22 ending with "plate".

In Column 4, line 23, please begin the paragraph by inserting --In this illumination apparatus, it is possible to irradiate two kinds of directional light and diffused light to an object to be detected, and therefore, even if the object to be detected is of a mirror surface shape or a concavity and convexity shape, it is possible to carry out appropriate illumination which corresponded to it, and it becomes possible to accordingly carry out stable detection. Furthermore, the directional light which irradiates the object to be detected, is generated by use of an annular light source and an annular reflection plate, and therefore it is possible to realize miniaturization with a simple configuration. Then,--.

In Column 4, line 33, please delete "(3)" and insert therefor --(2)--.

In Column 4, line 42, please delete "(4)" and insert therefor --(3)--.

UNITED STATES PATENT AND TRADEMARK OFFICE
CERTIFICATE OF CORRECTION

| | |
|---|---|
| PATENT NO. | : 7,502,170 B2 |
| APPLICATION NO. | : 10/523871 |
| DATED | : March 10, 2009 |
| INVENTOR(S) | : Kazuyuki Nakano et al. |

It is certified that error appears in the above-identified patent and that said Letters Patent is hereby corrected as shown below:

In Column 4, line 43, please delete "(2) or (3)" and insert therefor --(1) or (2)--.

In Column 4, line 56, please delete "(5)" and insert therefor --(4)--.

In Column 4, line 57, please delete "(1) through (3)" and insert therefor --(1) or (2)--.

In Column 5, line 1, please delete "(6)" and insert therefor --(5)--.

In Column 5, line 2, please delete "(5)" and insert therefor --(4)--.

In Column 5, line 9, please delete "(7)" and insert therefor --(6)--.

In Column 5, line 11, please delete "(6)" and insert therefor --(5)--.

In Column 5, line 23, please delete "(8)" and insert therefor --(7)--.

In Column 5, line 35, please delete "(7)" and insert therefor --(6)--.

In Column 5, line 41, please delete "(9)" and insert therefor --(8)--.

In Column 5, line 51, please delete "(7)" and insert therefor --(6)--.

In Column 6, line 65, please end the sentence with a period --.-- after the word "surface" and before "In".

In Column 7, line 17, please end the sentence with a period --.-- after the word "detected".

UNITED STATES PATENT AND TRADEMARK OFFICE
CERTIFICATE OF CORRECTION

PATENT NO. : 7,502,170 B2
APPLICATION NO. : 10/523871
DATED : March 10, 2009
INVENTOR(S) : Kazuyuki Nakano et al.

It is certified that error appears in the above-identified patent and that said Letters Patent is hereby corrected as shown below:

In Column 7, line 41, please delete "thoughholes" and insert therefor --through-holes--.

In Column 8, line 10, please delete (second occurrence) "L2" and insert therefor --L1--.

In Column 10, line 24, please end the sentence with a period --.-- after the word "direction" and before the word "In".

In Coloumn 10, line 57, please delete "391" and insert therefor --39--.

Signed and Sealed this

Second Day of June, 2009

JOHN DOLL
*Acting Director of the United States Patent and Trademark Office*